(12) United States Patent
Baxter et al.

(10) Patent No.: US 7,143,642 B1
(45) Date of Patent: Dec. 5, 2006

(54) INTEGRATED MOISTURE, LENGTH, AND STRENGTH TESTER

(75) Inventors: Preston S. Baxter, Friendsville, TN (US); James T. Wender, Seymour, TN (US); Muhammad Imran Sharafat, Knoxville, TN (US); Youe T. Chu, Knoxville, TN (US); Joe H. Mansfield, Knoxville, TN (US); Michael E. Galyon, Knoxville, TN (US); Hossein M. Ghorashi, Knoxville, TN (US)

(73) Assignee: Uster Technologies, Inc., Knoxville, TN (US)

( * ) Notice: Subject to any disclaimer, the term of this patent is extended or adjusted under 35 U.S.C. 154(b) by 33 days.

(21) Appl. No.: 11/173,571

(22) Filed: Jul. 1, 2005

(51) Int. Cl.
*G01L 4/04* (2006.01)
(52) U.S. Cl. .................................................. 73/159
(58) Field of Classification Search ................. 73/159, 73/160, 866; 700/142; 19/66 CC, 65 R, 19/66 R; 356/73.1
See application file for complete search history.

(56) References Cited

U.S. PATENT DOCUMENTS

| | | | |
|---|---|---|---|
| 2,706,403 A * | 4/1955 | Hertel | 73/834 |
| 3,591,294 A * | 7/1971 | Neil | 356/147 |
| 4,088,016 A * | 5/1978 | Watson et al. | 73/160 |
| 5,269,181 A * | 12/1993 | Gibson et al. | 73/160 |
| 5,270,787 A * | 12/1993 | Shofner et al. | 356/429 |
| 5,596,901 A * | 1/1997 | Gloor | 73/159 |
| 5,611,238 A * | 3/1997 | Bader et al. | 73/160 |
| 5,799,103 A * | 8/1998 | Schneider et al. | 382/141 |
| 5,907,394 A * | 5/1999 | Ghorashi et al. | 356/73.1 |
| 6,112,131 A * | 8/2000 | Ghorashi et al. | 700/142 |
| 6,161,441 A * | 12/2000 | Ghorashi et al. | 73/863.92 |
| 6,532,798 B1 * | 3/2003 | Shofner et al. | 73/38 |
| 6,598,267 B1 * | 7/2003 | Shofner et al. | 19/66 CC |
| 2006/0179932 A1* | 8/2006 | Ramachandran et al. | 73/160 |

* cited by examiner

*Primary Examiner*—Hezron Williams
*Assistant Examiner*—John Fitzgerald
(74) *Attorney, Agent, or Firm*—Luedeka, Neely, & Graham, P.C.

(57) ABSTRACT

A fiber testing station. Electrically conductive first fiber retaining means engage first ends of fibers, where the fibers extend in substantially one direction from the first fiber retaining means to distal second ends of the retained fibers. The first fiber retaining means are electrically isolated from the fiber testing station. First length measurement means measure first relaxed lengths of the retained fibers between the first fiber retaining means and the second ends of the retained fibers. Electrically conductive second fiber retaining means engage the second ends of the retained fibers. The second fiber retaining means are electrically isolated from the fiber testing station. Moisture measurement means take electrical measurements along the retained fibers between the first fiber retaining means and the second fiber retaining means, and thereby determine a moisture content of the retained fibers. Tension means pull the first fiber retaining means and the second fiber retaining means away from one another, and thereby stretch the retained fibers until the retained fibers break at a fracture point.

14 Claims, 6 Drawing Sheets

INTEGRATED MOISTURE, LENGTH, AND STRENGTH TESTER

FIELD

This invention relates to the field of fiber testing. More particularly, this invention relates to measuring the moisture content, length, and strength of cotton fibers.

BACKGROUND

Several factors effect how cotton or other fibers are graded or classed. For example, some of the factors that affect the grade assigned to cotton fibers are the moisture content of the sample, the length of the cotton fibers, the tensile strength of the cotton fibers, the color of the fibers, and the trash content of the cotton. Thus, various tests are often conducted on different fiber samples to determine these factors. Once the factors are determined, the fiber can be classed. These factors can also be used to set processing parameters for the fibers.

Some of these factors are dependent one upon another. For example, the length and strength of the fibers tends to be dependent at least in part upon the moisture content of the sample. Generally, the length and strength of fibers tend to increase as the moisture content of the sample increases—at least up to a point. For this reason, a given sample may be humidity conditioned for a specified period of time before the tests are conducted, so that the tests are performed at some known or assumed moisture value. In this manner, the length and strength readings can be correlated between fiber samples.

However, it is not always practical to humidify a sample prior to testing. For example, it may be desirable to know the actual moisture content of the sample, and not condition the sample to some baseline moisture value. When such testing is desired, different fiber samples are typically pulled and sent to different pieces of inspection equipment for the various tests desired, such as length, strength, and moisture content.

Unfortunately, as mentioned above, the length and strength of the fibers tends to be dependent, at least in part, on the moisture content of the fibers. Because the moisture content can vary from one fiber sample to another, there is no guarantee that the moisture content of the sample sent for moisture analysis is the same as the moisture content of the sample sent for strength analysis, or the same as that of the sample sent for length analysis. Thus, the values determined for length and strength might not be readily comparable to values determined for other samples, because the moisture content of the length and strength samples might not really be known.

What is needed, therefore, is a system of testing that overcomes problems such as those described above, at least in part.

SUMMARY

The above and other needs are met by a fiber testing station having moisture testing means, and at least one of strength testing means, and length testing means, where the moisture testing means and the at least one of the strength testing means and the length testing means have common fiber sample engagement components, and are disposed within a common testing site that operates on a single fiber sample, such that the fiber sample is not transported between any of the moisture testing means and the at least one of the strength testing means and the length testing means.

In this manner, at least one of length and strength readings are taken on the same fiber sample that is used for the moisture testing. Thus, the moisture content of the sample is known, and the length and strength readings on the sample can be correlated with the actual moisture content. Further, these measurements are taken in a highly integrated fashion, where a single testing device can be used to take all three readings.

In one embodiment, electrically conductive first fiber retaining means engage first ends of fibers, where the fibers extend in substantially one direction from the first fiber retaining means to distal second ends of the retained fibers. The first fiber retaining means are electrically isolated from the fiber testing station. First length measurement means measure first relaxed lengths of the retained fibers between the first fiber retaining means and the second ends of the retained fibers. Electrically conductive second fiber retaining means engage the second ends of the retained fibers. The second fiber retaining means are electrically isolated from the fiber testing station. Moisture measurement means take electrical measurements along the retained fibers between the first fiber retaining means and the second fiber retaining means, and thereby determine a moisture content of the retained fibers. Tension means pull the first fiber retaining means and the second fiber retaining means away from one another, and thereby stretch the retained fibers until the retained fibers break at a fracture point. Second length measurement means measure second tracted lengths of the retained fibers at the fracture point.

In various embodiments of the invention, the first length measurement means and the second length measurement means are one measurement means. In one embodiment the tension means pulls the second fiber retaining means away from the first fiber retaining means while the first fiber retaining means remain stationary. In some embodiments the first length measurement means include a linear array of light sensors disposed on a first side of the retained fibers and at least one light disposed on a second opposing side of the retained fibers. The second length measurement means are, in some embodiments, attached to the tension means and measure a distance between the first fiber retaining means and the second fiber retaining means as they are pulled away from one another. A vacuum port may draw a flow of air from the first fiber retaining means through the first length measurement means to draw the retained fibers into the first length measurement means.

According to another aspect of the invention there is described a method of testing fibers by engaging first ends of fibers with electrically conductive first fiber retaining means. The fibers extend in substantially one direction from the first fiber retaining means to distal second ends of the retained fibers. The first fiber retaining means are electrically isolated from the fiber testing station. First relaxed lengths of the retained fibers are measured between the first fiber retaining means and the second ends of the retained fibers with first length measurement means. The second ends of the retained fibers are engaged with electrically conductive second fiber retaining means. The second fiber retaining means are electrically isolated from the fiber testing station. Electrical measurements are taken along the retained fibers between the first fiber retaining means and the second fiber retaining means with moisture measurement means, and a moisture content of the retained fibers is thereby determined. The first fiber retaining means and the second fiber retaining means are pulled away from one another with tension means, and the retained fibers are thereby stretched until the retained fibers break at a fracture point. Second tracted lengths of the retained fibers at the fracture point are measured with second length measurement means.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
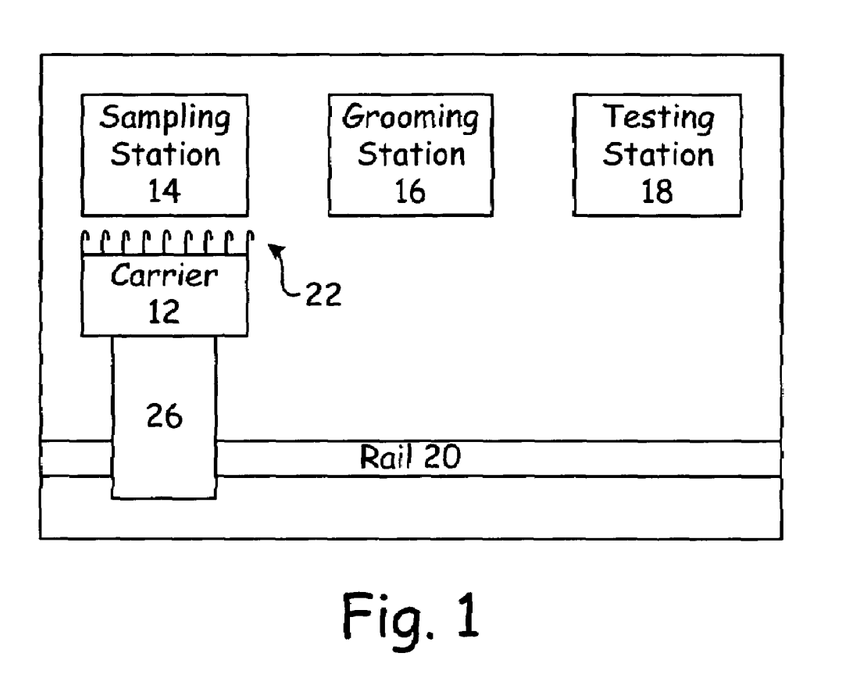
FIG. 1 is a functional block diagram of an apparatus according to a preferred embodiment of the present invention, with a fiber sampler in a first position.

With reference now to FIG. 1, there is depicted a fiber tester 10. The fiber tester 10 preferably has three basic stations, including a sampling station 14, a grooming station 16, and a testing station 18. The fiber sample is preferably drawn from the sampling station 14, such as by a comb 22 on a carrier 12. The carrier 12 is brought into proximity with the sampling station 14, and the other stations 16 and 18, such as by a stage 26 that can move back and forth. In an alternate embodiment, the carrier 12 maintains its position, and the sampling station 14 is brought into position adjacent the carrier 12, such as by mounting the station 14 on a stage 26. Thus, either one or both of the carrier 12 and the stations 12, 16, or 18 at which it is placed may be moved so as to engage the carrier 12 with the station. Further, at some stations the carrier 12 may move to the station, and at other stations the station may move to the carrier 12. For simplicities sake, the following examples state that the carrier 12 moves to the station, but it is understood that this description is not by way of limitation.

Figure 2:
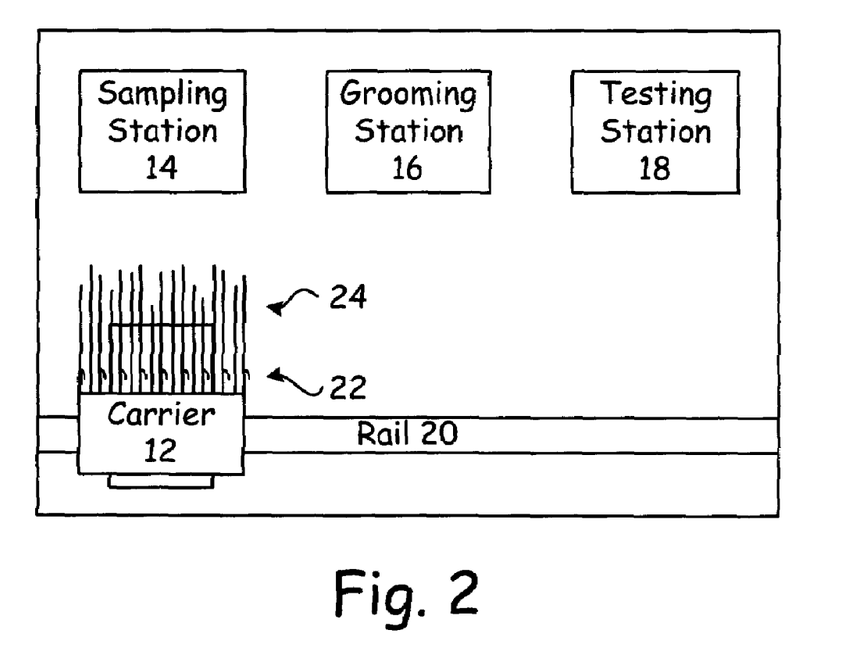
FIG. 2 is a functional block diagram of an apparatus according to a preferred embodiment of the present invention, with the fiber sampler having acquired a fiber sample.

In any of the embodiments discussed above, the carrier 12 preferably rides along a rail 20 that enables the carrier 12 to move from station to station within the fiber tester 10. FIG. 2 depicts the carrier 12 in the retracted position, with fibers 24 caught in the comb 22. In this configuration, the fibers 24 are also referred to as a beard 24.

Figure 3:
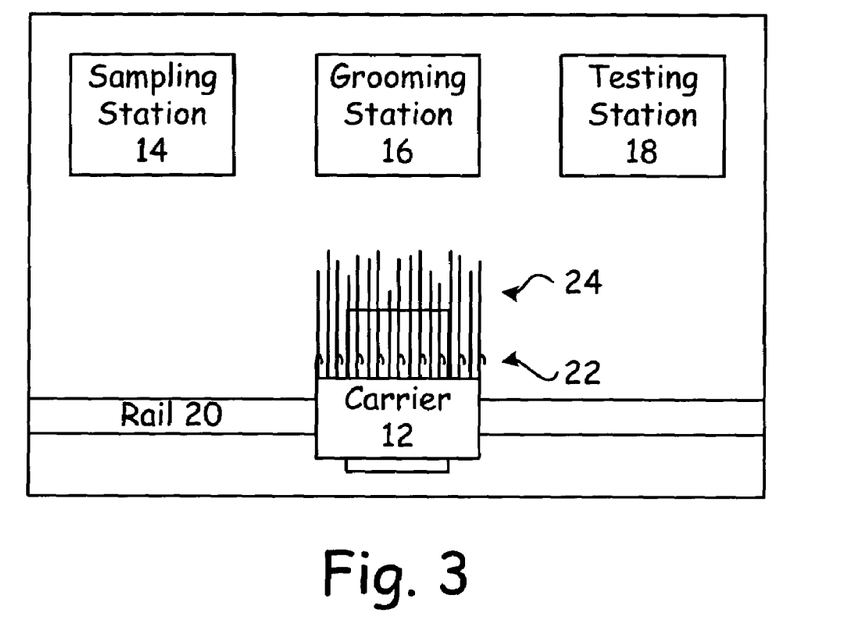
FIG. 3 is a functional block diagram of an apparatus according to a preferred embodiment of the present invention, with the fiber sampler in a second position.
Figure 4:
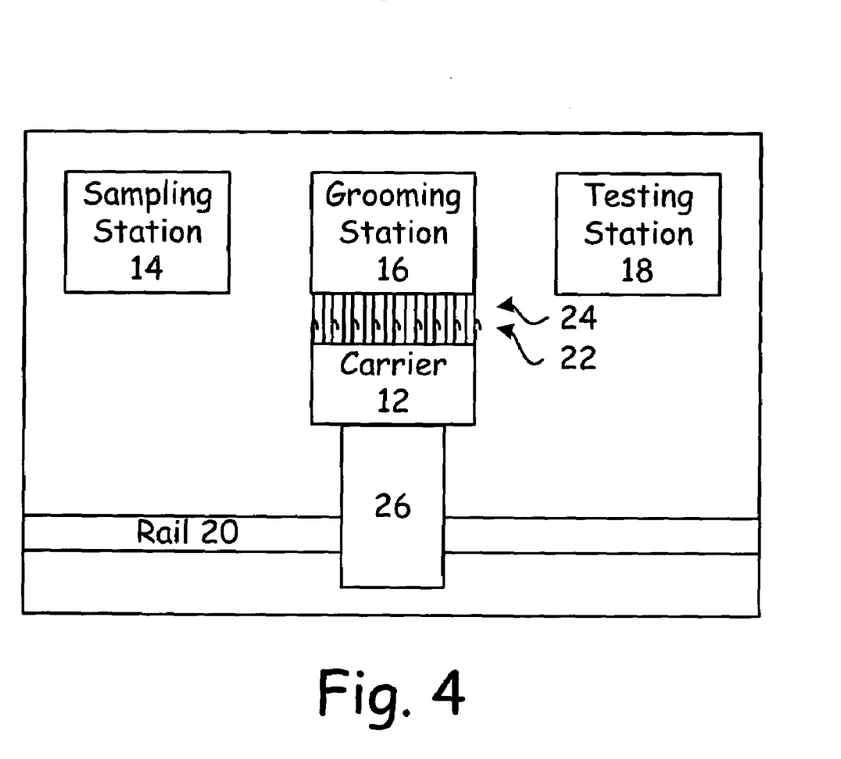
FIG. 4 is a functional block diagram of an apparatus according to a preferred embodiment of the present invention, with the fiber sample being groomed.

The carrier 12 is preferably moved along the rail 20 to the second position as depicted in FIG. 3, and the stage 26 is extended to the grooming station 16, where the beard 24 is brushed or otherwise prepared for testing, as depicted in FIG. 4. This preparation process preferably somewhat straightens and parallelizes the individual fibers of the beard 24, in preparation for testing.

Figure 5:
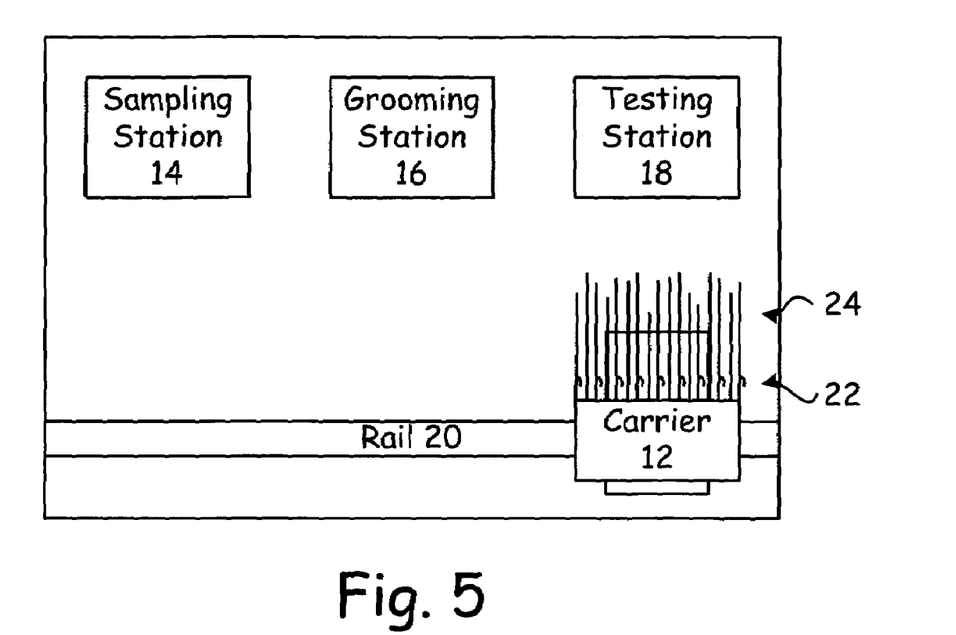
FIG. 5 is a functional block diagram of an apparatus according to a preferred embodiment of the present invention, with the fiber sampler in a third position.

The carrier 12 is then retracted back towards the rail 20 on the stage 26, and indexed to the third position, as depicted in FIG. 5. The carrier 12 is then extended toward the testing station 18 on the stage 26, where the beard 24 is tested. FIGS. 7–12 depict a series of preferred steps in the testing process. The functions and construction of this single testing station 18 are predominantly discussed in the description provided below.

Figure 7:
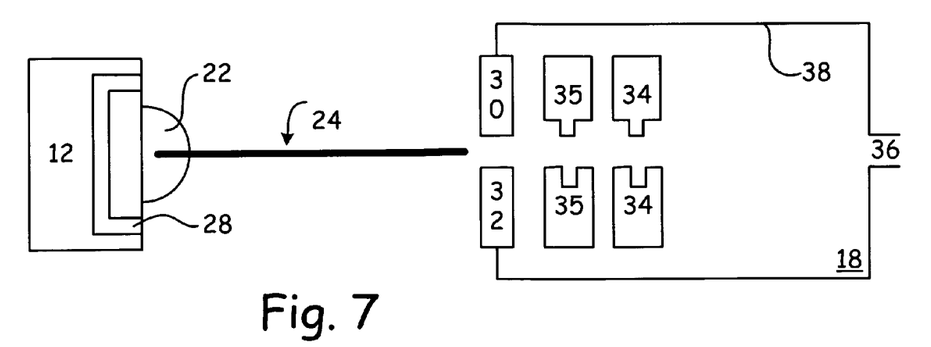
FIG. 7 is a functional block diagram of a fiber tester according to a preferred embodiment of the present invention, with the fiber sample outside the fiber tester.

As depicted in FIG. 7, with the carrier 12 in the retracted position, such as that depicted in FIG. 5, the beard 24 preferably does not extend within the testing station 18. As depicted in greater detail in FIG. 7, the carrier 12 may be electrically isolated from the comb 22, such as by a non electrically conductive layer 28. The comb 22, or other means that are used to engage the ends of the fibers 24, is preferably electrically conductive. The significance of the electrical conductivity of the comb 22 and its possible electrical isolation from the other elements of the system 10 are described in more detail hereafter.

Figure 6:
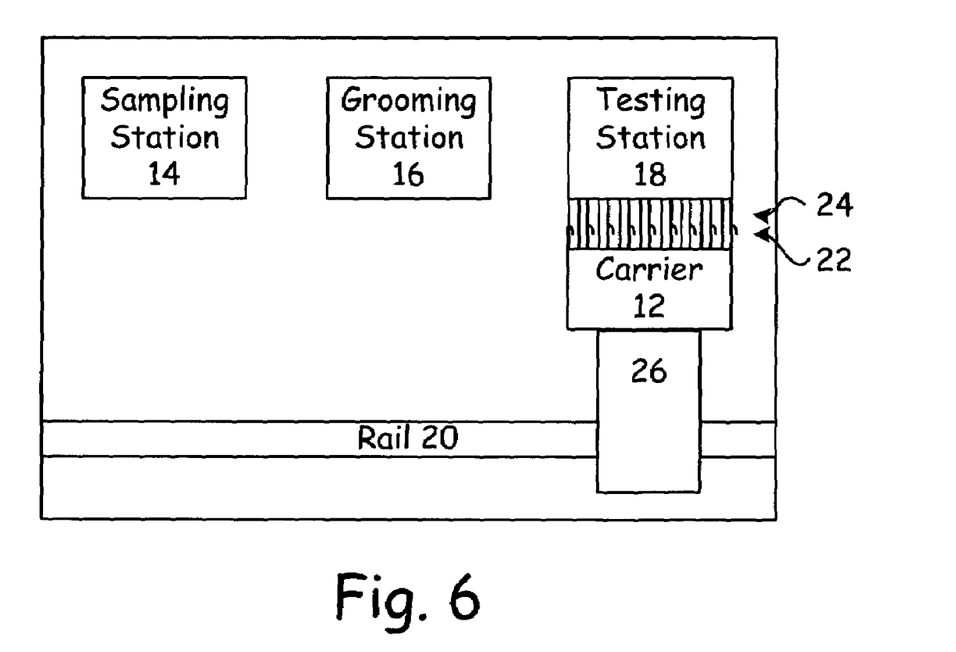
FIG. 6 is a functional block diagram of an apparatus according to a preferred embodiment of the present invention, with the fiber sample being tested.
Figure 8:
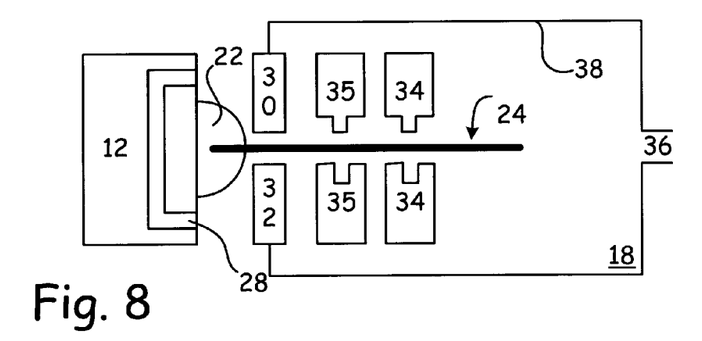
FIG. 8 is a functional block diagram of a fiber tester according to a preferred embodiment of the present invention, with the fiber sample inside the fiber tester.
Figure 9:
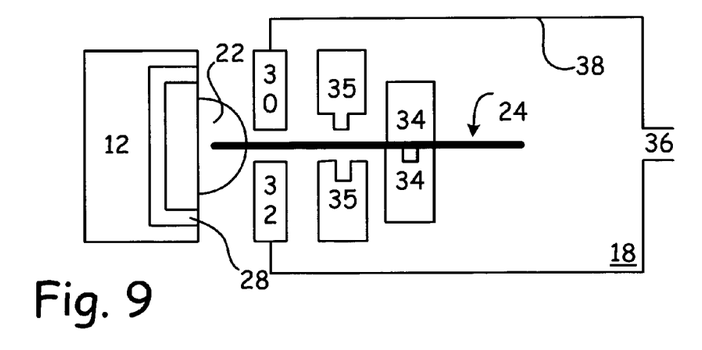
FIG. 9 is a functional block diagram of a fiber tester according to a preferred embodiment of the present invention, with the fiber sample clamped inside the fiber tester.

The testing station 18 preferably includes a housing 38, which separates the interior elements of the testing station 18 from the other elements of the system 10. To perform the tests, the carrier 12 and the testing station 18 are moved toward each other as depicted in FIGS. 6 and 8. As mentioned above, either one or both of the carrier 12 and the testing station 18 could be moved to provide this engagement between the carrier 12 and the testing station 18. As this is done, the beard 24 preferably extends within the testing station 18, such as through a slot in the housing 38. In some embodiments, a draft of air, such as drawn through vacuum port 36, assists the beard 24 in entering the testing station 18.

Figure 13:
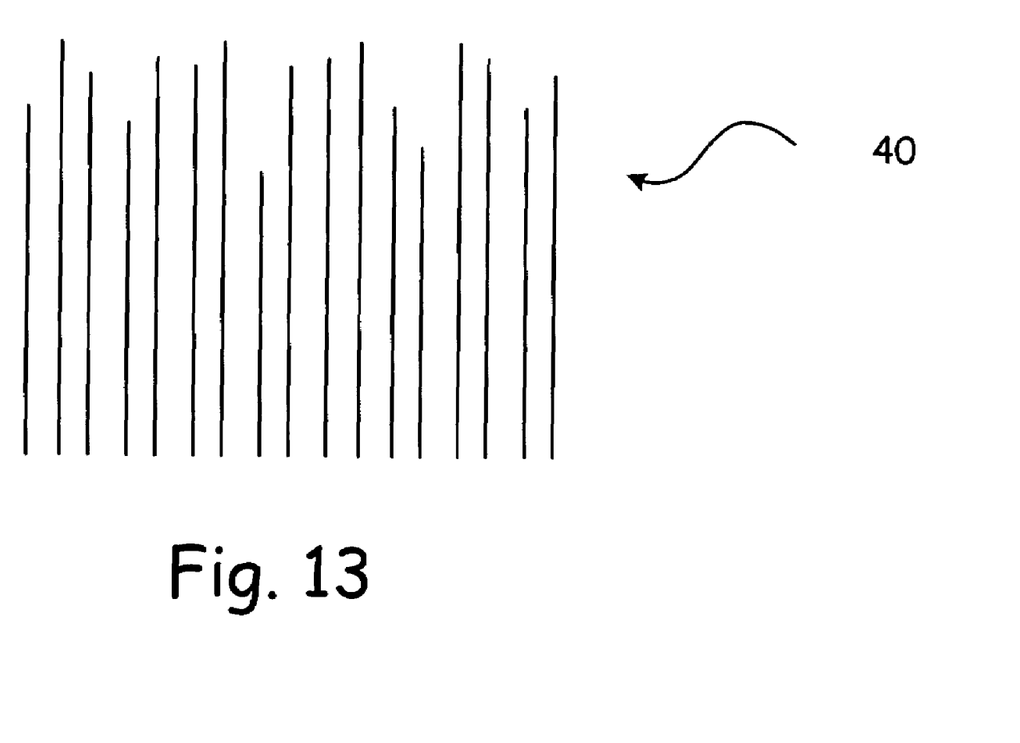
FIG. 13 is a graph of fiber lengths within the fiber sample.

The beard 24 is preferably measured as it enters the testing station 18. This is most preferably accomplished by measurement means 30 and 32. In the preferred embodiments, measurement means 30 and 32 are a linear series of sensors, such as light sensors, on one side of the beard 24, and a light, such as a linear series of light emitting diodes, on the other side of the beard 24. Thus, as the beard 24 enters the testing station 18 through the slot, the individual fibers of the beard 24 block the light passing between the measurement means 30 and 32. This blockage can be detected with the sensors, and correlated with the position of the carrier 12 on the stage 26 to determine the various lengths of the fibers in the beard 24, such as with a graphical plot 40 as depicted in FIG. 13. Thus, the length of the fibers in the beard 24 is preferably determined when the beard 24 is inserted into the testing station 18.

Once the beard 24 has been inserted into the testing station 18, and the length of the fibers 24 preferably determined, the beard 24 is preferably retained on the end inserted within the testing station 18, such as by jaws 34. The jaws 34 are preferably electrically conductive and, similar to that described above in regard to the comb 22, may also be electrically isolated from the rest of the system 10. Electrical connections are preferably provided between the jaws 34 and the comb 22 to an electrical testing apparatus, which is used to determine the moisture content in the beard 24 between the comb 22 and the jaws 34. At least one of the jaws 34 and the comb 22 are preferably electrically isolated from the rest of the system 10 so that this electrical test can be conducted to determine the moisture content of the beard 24. In one embodiment, one of the jaws 34 and the comb 22 are electrically isolated from the rest of the system 10, and the other is grounded with the rest of the system 10. In another embodiment, both the jaws 34 and the comb 22 are electrically isolated from the system. Most preferably, a method such as one based on the electrical resistance of the beard 24 between the comb 22 and the jaws 34 is used to determine the moisture content of the beard 24.

Figure 10:
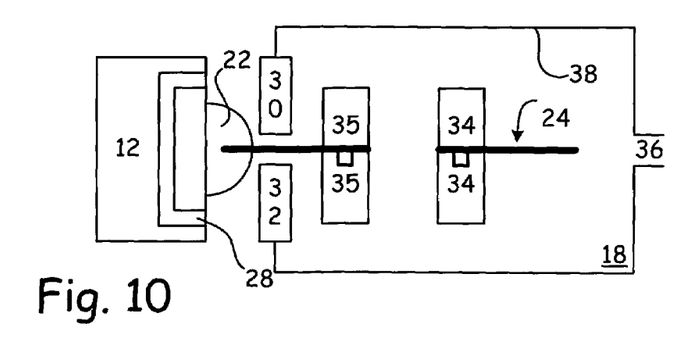
FIG. 10 is a functional block diagram of a fiber tester according to a preferred embodiment of the present invention, with the fiber sample broken by moving the clamp inside the fiber tester.
Figure 11:
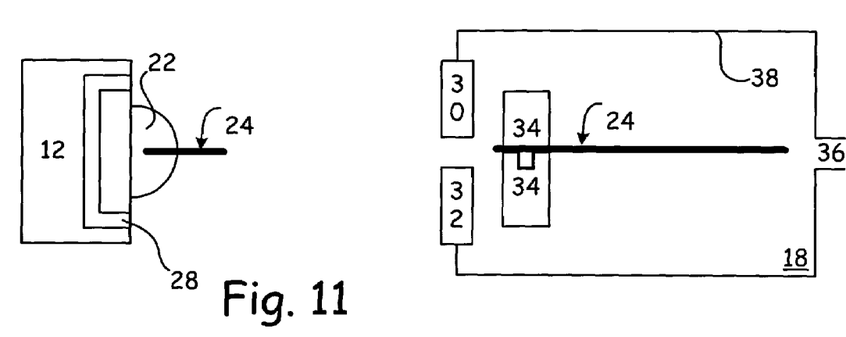
FIG. 11 is a functional block diagram of a fiber tester according to an alternate embodiment of the present invention, with the fiber sample broken by moving the fiber sampler.
Figure 12:
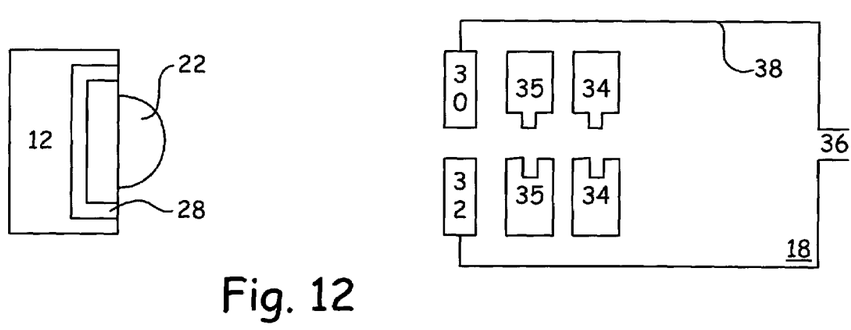
FIG. 12 is a functional block diagram of a fiber tester according to a preferred embodiment of the present invention, with the broken fiber sample expelled.

After the moisture content of the beard 24 is measured, a second set of jaws 35 is clamped on the beard 24, and the jaws 35 and the jaws 34 are preferable pulled apart, one from another. As depicted in FIG. 10, this pulling is accomplished by retracting the jaws 34 away from the jaws 35. The pulling could also be accomplished by retracting at least one of the comb 22 and the jaws 34 away from each other, without the use of the jaws 35, as depicted in FIG. 11. The separation is preferably continued until the beard 24 breaks, as depicted in both FIGS. 10 and 11.

It is appreciated that the time at which the second set of jaws 35 is clamped onto the beard 24 can vary, from one embodiment to another. For example, if the jaws 35 are electrically isolated or non electrically conducting, then they can be clamped onto the beard 24 prior to taking the moisture measurement on the beard 24. Further, the stretching and breaking of the fibers 24 can be accomplished between any two of the comb 22, jaws 34, and jaws 35, in various embodiments.

A variety of measurements can be taken during this breaking process. For example, the force required to separate the jaws 35 and the jaws 34 can be measured during the breaking process. Further, the distance by which the beard 24 was stretched or elongated prior to breaking can also be measured, as determined by the distance by which the jaws 35 and the jaws 34 were separated during the breaking process. Either or both of these measurements can be used to determine a strength value for the fibers 24, which strength measurement is the third measurement to be taken by the testing station 18.

Once two or more of the three measurements have been taken as desired, the two ends of the broken beard of fibers 24 are preferably released from the comb 22 and the jaws 34 and discarded, and the carrier 12 is preferably cycled back to the first position as depicted in FIG. 1 to start the sampling, grooming, and testing process anew with another fiber sample.

In this manner, the testing station 18 is adapted to take three measurements on the fibers 24, which three measurements are length, moisture content, and strength. All three measurements can be taken on the same beard of fibers 24. Thus, the length and strength of the fibers 24 can be correlated to the moisture content of the fibers 24, as determined from the same beard of fibers 24. As mentioned above, because the length and strength of the fibers 24 both tend to be dependent at least in part on the moisture content of the fibers 24, measurement of all three factors on the same beard 24 tends to produce more accurate correlations and measurements. Further, by performing all three measurements within a single testing station 18, the tests can be performed in a very time efficient manner.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A fiber testing station comprising:
   moisture testing means, and
   at least one of
      strength testing means, and
      length testing means,
   where the moisture testing means and the at least one of the strength testing means and the length testing means have common fiber sample engagement components, and are disposed within a common testing site that operates on a single fiber sample, such that the fiber sample is not transported between any of the moisture testing means and the at least one of the strength testing means and the length testing means as testing is performed.

2. The fiber testing station of claim 1, further comprising a single fiber retaining means in which the fiber sample is retained while moisture testing and at least one of strength testing and length testing are performed on the fiber sample.

3. A fiber testing station comprising:
   electrically conductive first fiber retaining means adapted to engage first ends of fibers, where the fibers extend in substantially one direction from the first fiber retaining means to distal second ends of the retained fibers,
   first length measurement means adapted to measure first relaxed lengths of the retained fibers between the first fiber retaining means and the second ends of the retained fibers,
   electrically conductive second fiber retaining means adapted to engage the second ends of the retained fibers while the first ends of the fibers remain engaged by the first fiber retaining means,
   at least one of the first fiber retaining means and the second fiber retaining means electrically isolated from the fiber testing station,
   moisture measurement means adapted to take electrical measurements along the retained fibers between the first fiber retaining means and the second fiber retaining means and thereby determine a moisture content of the retained fibers,
   tension means adapted to stretch the retained fibers using the second fiber retaining means until the retained fibers break at a fracture point, and second length measurement means adapted to measure second tracted lengths of the retained fibers at the fracture point.

4. The fiber testing station of claim 3, wherein the first length measurement means and the second length measurement means are one measurement means.

5. The fiber testing station of claim 3, wherein the tension means pulls the second fiber retaining means away from a third fiber retaining means while the third fiber retaining means remain stationary.

6. The fiber testing station of claim 3, wherein the first length measurement means include a linear array of light sensors disposed on a first side of the retained fibers and at least one light disposed on a second opposing side of the retained fibers.

7. The fiber testing station of claim 3, wherein the second length measurement means are attached to the tension means and measure a distance between the first fiber retaining means and the second fiber retaining means as the second fiber retaining means break the fibers.

8. The fiber testing station of claim 3, further comprising a vacuum port adapted to draw a flow of air from the first fiber retaining means through the first length measurement means to draw the retained fibers into the first length measurement means.

9. A method of testing fibers, the method comprising the steps of:
engage first ends of fibers with electrically conductive first fiber retaining means, where the fibers extend in substantially one direction from the first fiber retaining means to distal second ends of the retained fibers,
measure first relaxed lengths of the retained fibers between the first fiber retaining means and the second ends of the retained fibers with first length measurement means,
engage the second ends of the retained fibers with electrically conductive second fiber retaining means,
where at least one of the first fiber retaining means and the second fiber retaining means are electrically isolated from the fiber testing station,
take electrical measurements along the retained fibers between the first fiber retaining means and the second fiber retaining means with moisture measurement means, and thereby determine a moisture content of the retained fibers,
stretch the retained fibers until the retained fibers break at a fracture point, and
measure a strength of the retained fibers with at least one of second tracted lengths of the retained fibers at the fracture point and a force required to fracture the retained fibers.

10. The method of claim 9, wherein the fibers are stretched by pulling the second fiber retaining means away from the first fiber retaining means while the first fiber retaining means remain stationary.

11. The method of claim 9, wherein the fibers are stretched by pulling the first fiber retaining means away from the second fiber retaining means while the first fiber retaining means remain stationary.

12. The method of claim 9, wherein the fibers are stretched by pulling the second fiber retaining means away from a third fiber retaining means while the first fiber retaining means and the third fiber retaining means remain stationary.

13. The method of claim 9, wherein the first length measurement means are a linear matrix of light sensors on a first side of the retained fibers and at least one light on a second opposing side of the retained fibers.

14. The method of claim 9, further comprising the step of drawing a flow of air from the first fiber retaining means through the first length measurement means to draw the retained fibers into the first length measurement means.

* * * * *